(12) United States Patent
Pilletere et al.

(10) Patent No.: US 11,998,235 B2
(45) Date of Patent: *Jun. 4, 2024

(54) TWO POINT CONTACT FLANGE FOR INSTRUMENT SEALS

(71) Applicant: Covidien LP, Mansfield, MA (US)

(72) Inventors: Roy Pilletere, Middletown, CT (US);
Garrett Ebersole, Hamden, CT (US);
Eric Brown, Madison, CT (US);
Matthew Dinino, Newington, CT (US);
Justin Thomas, New Haven, CT (US);
Jacob Baril, Norwalk, CT (US);
Nicolette LaPierre, Windsor Locks, CT (US)

(73) Assignee: Covidien LP, Mansfield, MA (US)

( * ) Notice: Subject to any disclaimer, the term of this patent is extended or adjusted under 35 U.S.C. 154(b) by 4 days.

This patent is subject to a terminal disclaimer.

(21) Appl. No.: 17/884,463

(22) Filed: Aug. 9, 2022

(65) Prior Publication Data

US 2022/0378471 A1 Dec. 1, 2022

Related U.S. Application Data

(63) Continuation of application No. 16/599,244, filed on Oct. 11, 2019, now Pat. No. 11,406,420.

(51) Int. Cl.
*A61B 17/34* (2006.01)

(52) U.S. Cl.
CPC ...... *A61B 17/3423* (2013.01); *A61B 17/3498* (2013.01); *A61B 2017/3486* (2013.01)

(58) Field of Classification Search
CPC ............ A61B 17/3423; A61B 17/3492; A61B 17/3462; A61B 2017/3486
See application file for complete search history.

(56) References Cited

U.S. PATENT DOCUMENTS

| | | | |
|---|---|---|---|
| 5,743,884 A | * | 4/1998 | Hasson ............. A61B 17/3462 604/249 |
| 5,895,377 A | | 4/1999 | Smith et al. |

(Continued)

FOREIGN PATENT DOCUMENTS

| | | |
|---|---|---|
| CN | 104083195 A | 10/2014 |
| EP | 3242615 A1 | 11/2017 |

(Continued)

OTHER PUBLICATIONS

Extended European Search Report issued in European Patent Application No. 20200998.1, dated Feb. 12, 2021.

*Primary Examiner* — Anu Ramana
(74) *Attorney, Agent, or Firm* — Carter, DeLuca & Farrell LLP

(57) ABSTRACT

An access assembly includes an instrument valve housing and a valve assembly disposed within the instrument valve housing. The instrument valve housing includes upper and lower housing sections. The valve assembly includes a centering mechanism, a seal assembly, and a guard assembly. The centering mechanism is configured to bias the valve assembly towards a generally centered position within the instrument valve housing. The centering mechanism includes a base seal member having an annular base and a flange portion. The flange portion includes an arcuate portion configured to adjustably engage first and second surfaces of the instrument valve housing in a sealing relation. The seal assembly is attachable to the centering mechanism. The seal assembly is configured to engage a surgical instrument inserted into the access assembly in a sealing relation. The guard assembly is attachable to the centering mechanism.

17 Claims, 7 Drawing Sheets

(56) References Cited

U.S. PATENT DOCUMENTS

| | | | |
|---|---|---|---|
| 6,569,120 B1 | 5/2003 | Green et al. | |
| 7,300,448 B2 | 11/2007 | Criscuolo et al. | |
| 8,029,475 B2 * | 10/2011 | Franer | A61B 17/3462 |
| | | | 604/167.01 |
| 9,615,852 B2 * | 4/2017 | Farin | A61B 17/3468 |
| 10,136,918 B2 * | 11/2018 | Farin | A61B 17/3423 |
| 10,568,660 B2 | 2/2020 | Zhou | |
| 10,653,449 B2 | 5/2020 | Main et al. | |
| 10,722,111 B2 * | 7/2020 | Adinolfi | A61B 1/32 |
| 10,856,903 B2 * | 12/2020 | Farin | A61B 17/3462 |
| 11,406,420 B2 | 8/2022 | Pilletere et al. | |
| 2008/0300545 A1 | 12/2008 | Hsieh | |
| 2015/0031958 A1 | 1/2015 | Kleyman | |
| 2015/0216560 A1 | 8/2015 | Holsten | |
| 2018/0021063 A1 | 1/2018 | Main et al. | |
| 2019/0059938 A1 | 2/2019 | Holsten | |
| 2019/0059944 A1 | 2/2019 | Holsten | |
| 2019/0142466 A1 | 5/2019 | Zhu | |
| 2020/0246043 A1 | 8/2020 | Holsten et al. | |

FOREIGN PATENT DOCUMENTS

| | | |
|---|---|---|
| WO | 9112838 A1 | 9/1991 |
| WO | 2012131746 A1 | 10/2012 |
| WO | 2016186905 A1 | 11/2016 |

* cited by examiner

TWO POINT CONTACT FLANGE FOR INSTRUMENT SEALS

CROSS-REFERENCE TO RELATED APPLICATION

The present application is a continuation of U.S. patent application Ser. No. 16/599,244 filed on Oct. 11, 2019, now U.S. Pat. No. 11,406,420, the entire contents of which are hereby incorporated by reference herein.

FIELD

The present disclosure relates to surgical access assemblies for minimally invasive surgery. More particularly, the present disclosure relates to seals for use with the surgical access assemblies.

BACKGROUND

In order to facilitate minimally invasive surgery, a working space must be created in the desired surgical space. An insufflation gas, typically $CO_2$, is introduced into the abdomen of the patient to create an inflated state called pneumoperitoneum. Surgical access assemblies are utilized to allow the introduction of surgical instrumentation and endoscopes (or other visualization tools). These surgical access assemblies maintain the pressure for the pneumoperitoneum, as they have one or more seals. Typically, a "zero-seal" in the surgical access assemblies seals a surgical access assembly in the absence of a surgical instrument therein, and an instrument seal seals around a surgical instrument that is inserted through the surgical access assembly.

Surgical procedures require a robust seal capable of adjusting to manipulation of surgical instrumentation extending through the surgical access assemblies without compromising seal integrity. Therefore, it would be beneficial to have a surgical access assembly with improved seal capability and durability.

SUMMARY

In accordance with an embodiment of the present disclosure, an access assembly includes an instrument valve housing and a valve assembly disposed within the instrument valve housing. The instrument valve housing includes upper and lower housing sections and defines a cavity. The valve assembly includes a centering mechanism, a seal assembly, and a guard assembly. The centering mechanism is configured to bias the valve assembly towards a generally centered position within the cavity of the instrument valve housing. The centering mechanism includes a base seal member having an annular base and a flange portion. The flange portion includes an arcuate portion configured to adjustably engage first and second surfaces of the instrument valve housing in a sealing relation. The seal assembly is attachable to the centering mechanism. The seal assembly is configured to engage a surgical instrument inserted into the access assembly in a sealing relation. The guard assembly is attachable to the centering mechanism. The guard assembly is configured to protect the seal assembly during insertion and manipulation of the surgical instrument.

In an embodiment, the first and second surfaces of the instrument valve assembly may be orthogonal to each other.

In another embodiment, the first and second surfaces of the instrument valve assembly may be distal and lateral surfaces of the instrument valve assembly, respectively.

In yet another embodiment, the base seal member of the centering mechanism may define a recess configured to receive the guard assembly in a superposed relation.

In an embodiment, the arcuate portion of the base seal member may include an inner segment and an outer segment extending radially outward from the inner segment. The inner and outer segments may define a gap therebetween.

In another embodiment, the valve assembly may further include a retainer frame assembly configured to secure the seal assembly and the guard assembly with the centering mechanism.

In yet another embodiment, the retainer frame assembly may include first, second, and third members. The first member may include pins extending through the guard assembly, the centering mechanism, the seal assembly, and the second member, and into the third member.

In an embodiment, the third member of the retainer frame assembly may include an annular portion defining an annular groove. The annular groove may be configured to secure the plurality of pins of the first member of the retainer frame assembly thereto.

In another embodiment, the centering mechanism may further include a radial retention member including an annular ring and a plurality of spokes circumferentially arranged about the annular ring. The plurality of spokes may be biased radially outward.

In an embodiment, the plurality of spokes may be compressible such that when compressed the arcuate portion of the base seal member engages the second surface of the upper housing section in a sealing relation.

In another embodiment, the guard assembly may include a plurality of petals defining a central opening. Adjacent petals may at least partially overlap in a circular manner to enable relative movement to enable enlarging the central opening.

In yet another embodiment, the seal assembly may include a plurality of seal segments defining an opening configured to receive a surgical instrument in a sealing relation. The plurality of seal segments may be arranged about the opening in which adjacent seal segments are at least partially overlapped to enable relative movement therebetween for adjustable engagement with the surgical instrument.

In still yet another embodiment, the plurality of seal segments of the seal assembly may define a substantially hexagonal body.

In an embodiment, respective peripheral portions of the guard assembly and the seal segment may be secured with the base seal member of the centering mechanism.

In accordance with another embodiment of the present disclosure, a valve assembly for use in an access assembly includes a retainer frame assembly including first and second members, a centering mechanism, and a seal assembly. The centering mechanism is configured to bias the valve assembly towards a generally centered position within an instrument valve housing of the access assembly. The centering mechanism includes a base seal member having an annular base and a flange portion. The flange portion includes an arcuate portion configured to adjustably engage first and second surfaces of the access assembly in a sealing relation. The seal assembly is attachable to the centering mechanism. The seal assembly is configured to engage a surgical instrument inserted into the access assembly in a sealing relation.

In an embodiment, the arcuate portion of the base seal member may be configured to adjustably engage the first and second surfaces of the access assembly that are orthogonal to each other.

In another embodiment, the base seal member of the centering mechanism may include third and fourth surfaces opposing each other. The seal assembly may be secured to the third surface.

In an embodiment, the arcuate portion of the base seal member may include inner and outer segments defining a gap therebetween.

In another embodiment, the valve assembly may further include a guard assembly configured to be secured to the fourth surface of the base seal member of the centering mechanism. The guard assembly may be configured to protect the seal assembly during insertion and manipulation of the surgical instrument.

In yet another embodiment, the centering mechanism may further include an annular ring and a plurality of spokes extending outwardly from the annular ring.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein.

DETAILED DESCRIPTION

Figure 1:
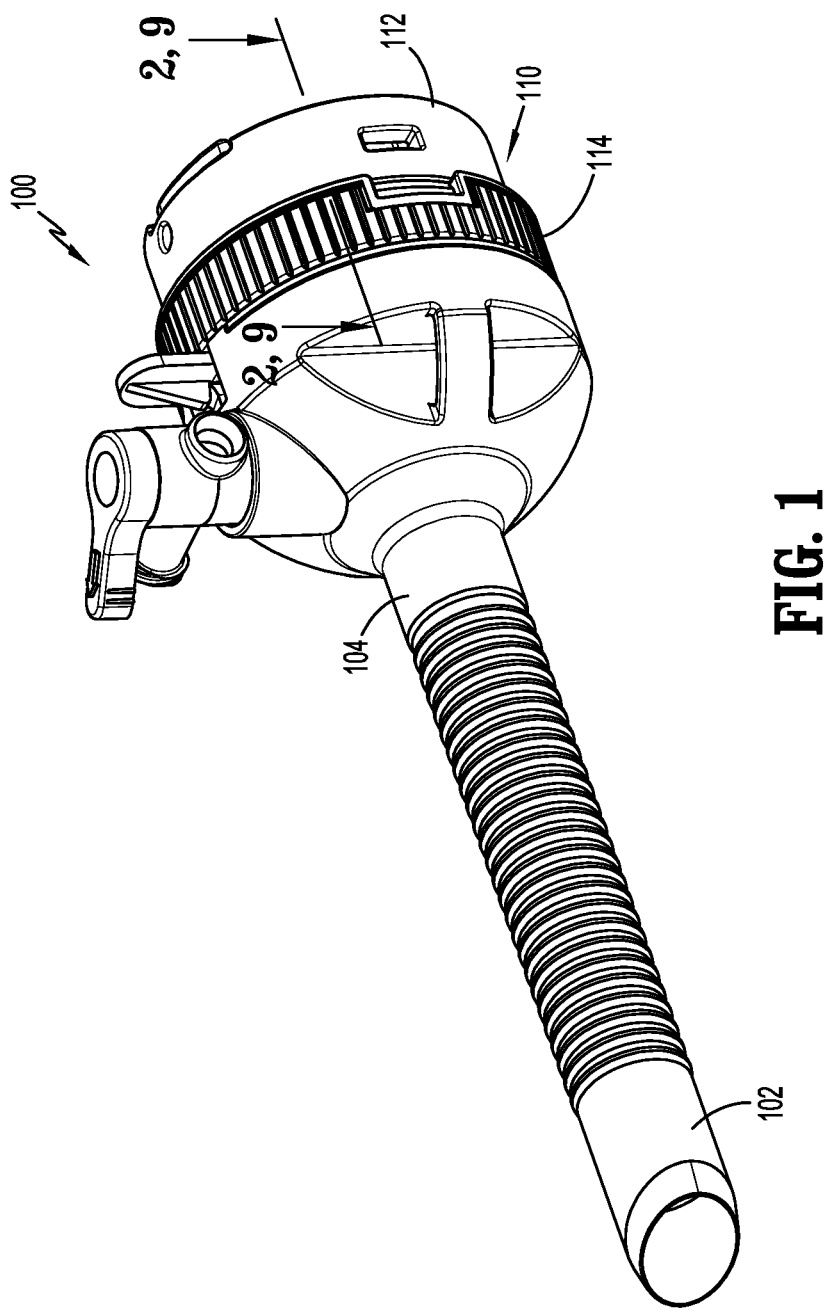
FIG. 1 is a perspective view of a surgical access assembly according to an embodiment of the present disclosure.

Particular embodiments of the present disclosure are described hereinbelow with reference to the accompanying drawings; however, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals refer to similar or identical elements throughout the description of the figures.

As used herein, the term "distal" refers to that portion of the instrument, or component thereof which is farther from the user while the term "proximal" refers to that portion of the instrument or component thereof which is closer to the user. As used herein, the term "about" means that the numerical value is approximate and small variations would not significantly affect the practice of the disclosed embodiments.

Figure 2:
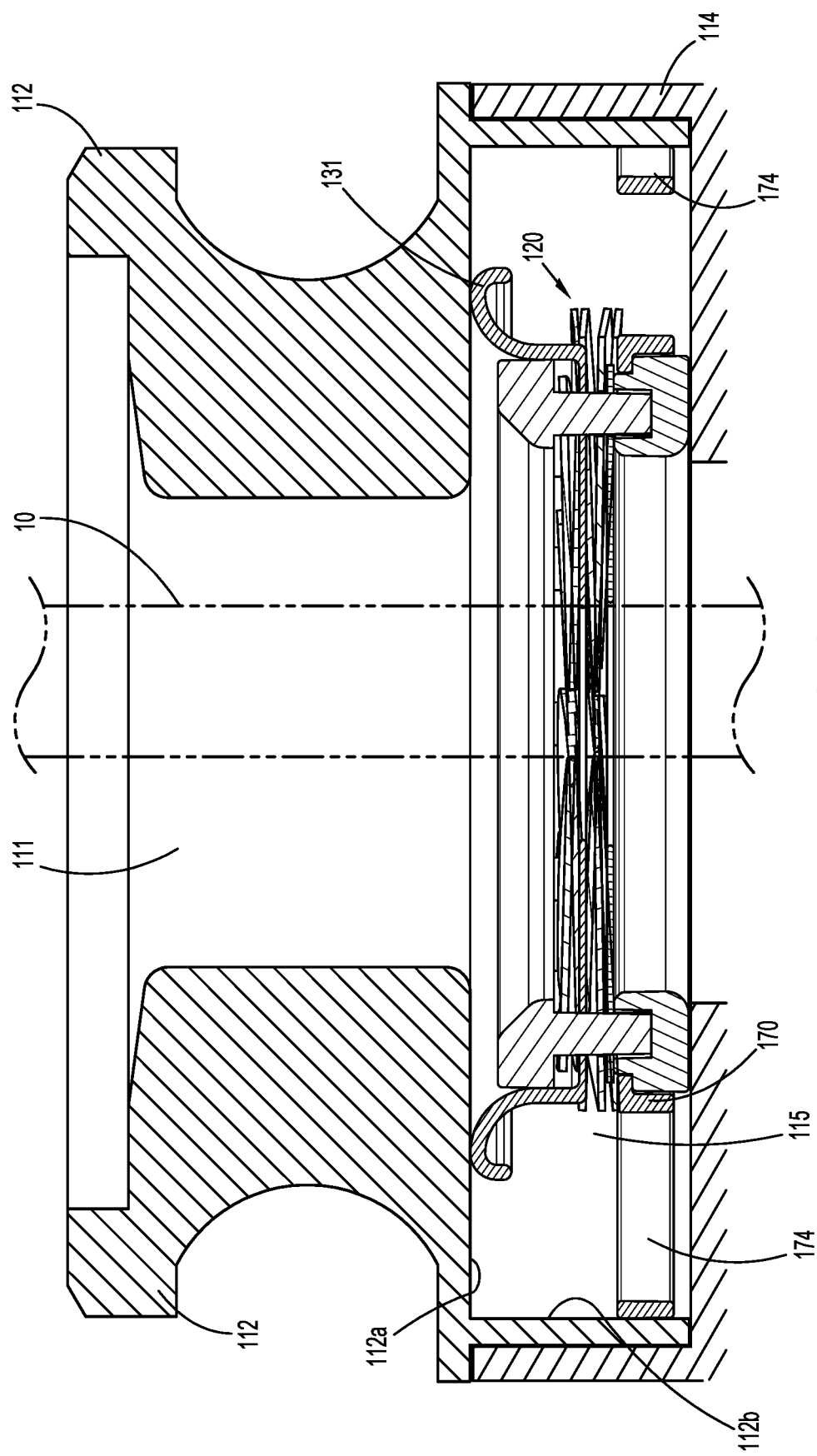
FIG. 2 is a cross-sectional side view of the surgical access assembly of FIG. 1 taken along section line 2-2 of FIG. 1.

With initial reference now to FIGS. 1 and 2, a surgical access assembly according to aspects of the present disclosure is shown generally as a cannula assembly 100. The cannula assembly 100 may be utilized during minimally invasive surgery, e.g., laparoscopic surgery, and provide for the sealed access of surgical instruments into an insufflated body cavity, such as the abdominal cavity. The cannula assembly 100 includes a cannula 102 and an instrument valve housing 110 secured to the cannula 102. The instrument valve housing 110 of the cannula assembly 100 includes an upper housing section 112 and a lower housing section 114. The upper and lower housing sections 112, 114 are configured to support a valve assembly 120 therein. The upper housing section 112 may be detachably secured with the lower housing section 114, and the lower housing section 114 may be releasably or permanently attached to a cannula tube 104 of the cannula assembly 102. In embodiments, the upper and/or lower housing sections 112, 114 of the instrument valve housing 110 may include, e.g., knurls, indentations, tabs, or be otherwise configured to facilitate engagement by a clinician. The upper and lower housing sections 112, 114 of the instrument valve housing 110 define a longitudinal passage 111 for receipt of a surgical instrument 10 (shown in phantom). The valve assembly 120 is supported within the instrument valve housing 110 to provide sealed passage of the surgical instrument 10 through the cannula assembly 100.

The cannula assembly 100 may be configured for use with an obturator (not shown) inserted through the instrument valve housing 110 and the cannula 102. The obturator may have a blunt distal end, or a bladed or non-bladed penetrating distal end. The obturator may be used to incise the abdominal wall so that the cannula assembly 100 may be introduced into the abdomen. The handle of the obturator may engage or selectively lock into the instrument valve housing 110 of the cannula assembly 100. For a detailed description of the structure and function of exemplary obturators and cannulas, reference may be made to commonly owned International Patent Publication No. WO 2016/186905 ("the '905 publication"), the contents of which are hereby incorporated by reference herein in its entirety.

In addition, the cannula assembly 100 may also include features for securement with a patient. For example, the distal end of the cannula tube 104 may support a balloon anchor or another expandable member that engages the abdomen from the interior side. A feature on the opposite side of the abdominal wall may be used to further stabilize the cannula assembly 100, such as adhesive tabs or adjustable foam collars. For a detailed description of such features on a cannula assembly, reference may be made to commonly owned U.S. Pat. No. 7,300,448, the entire disclosure of which is hereby incorporated by reference herein.

Figure 3:
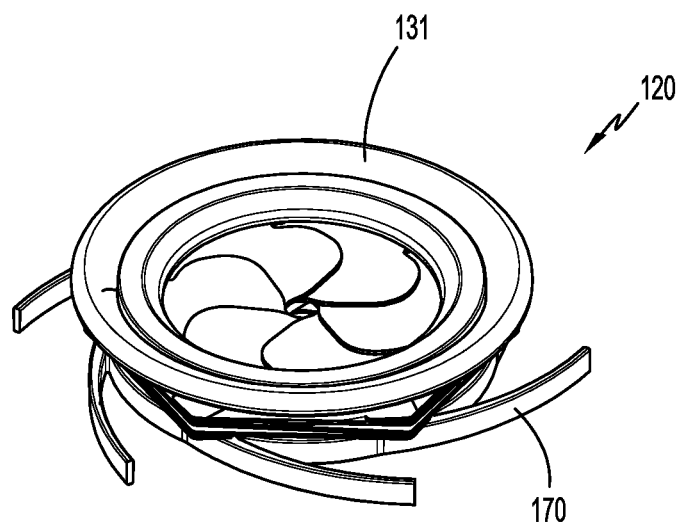
FIG. 3 is a top perspective view of a valve assembly of the surgical access assembly of FIG. 1 in accordance with an embodiment of the present disclosure.
Figure 4:
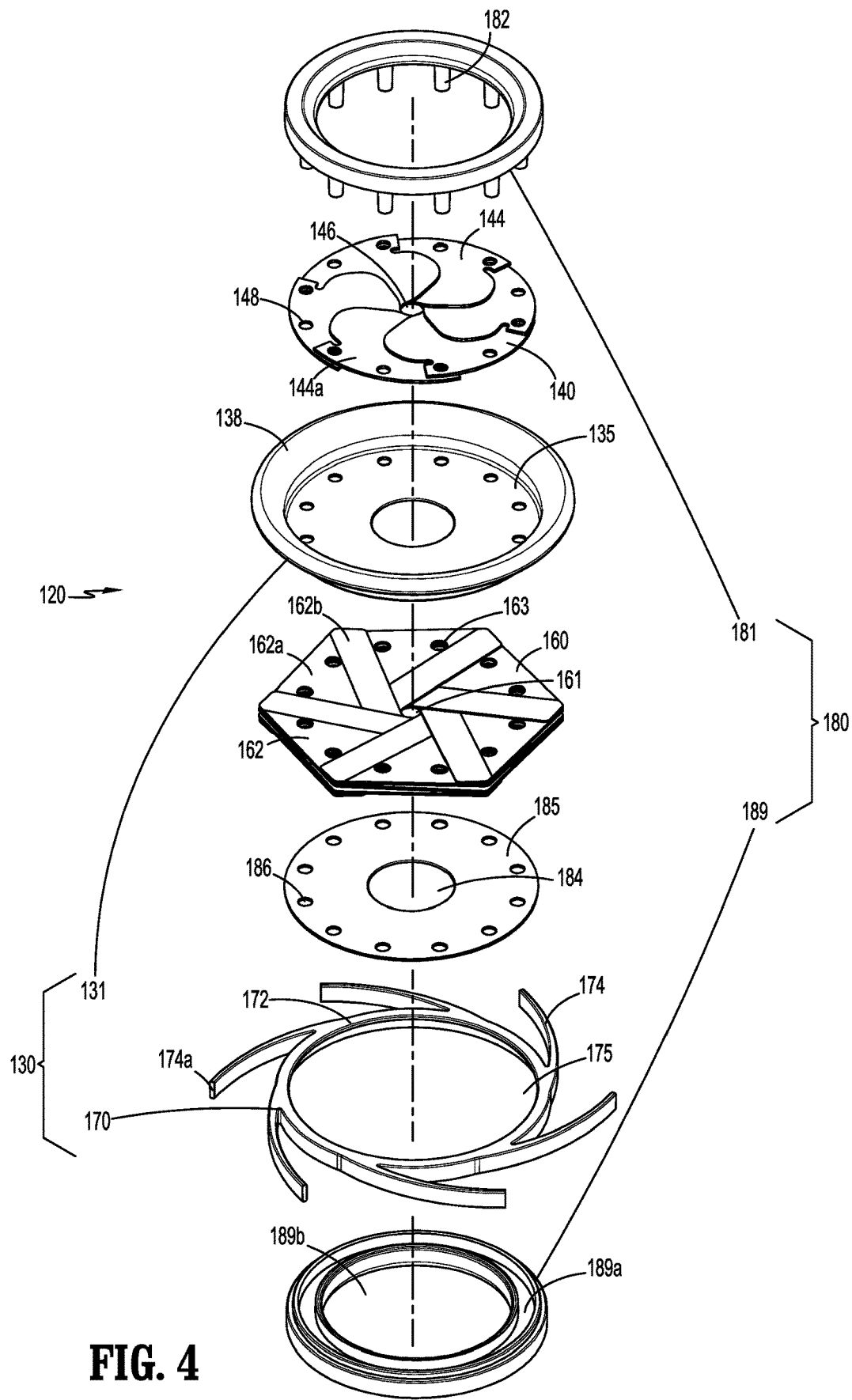
FIG. 4. is an exploded perspective view of the valve assembly of FIG. 3 with parts separated.
Figure 5:
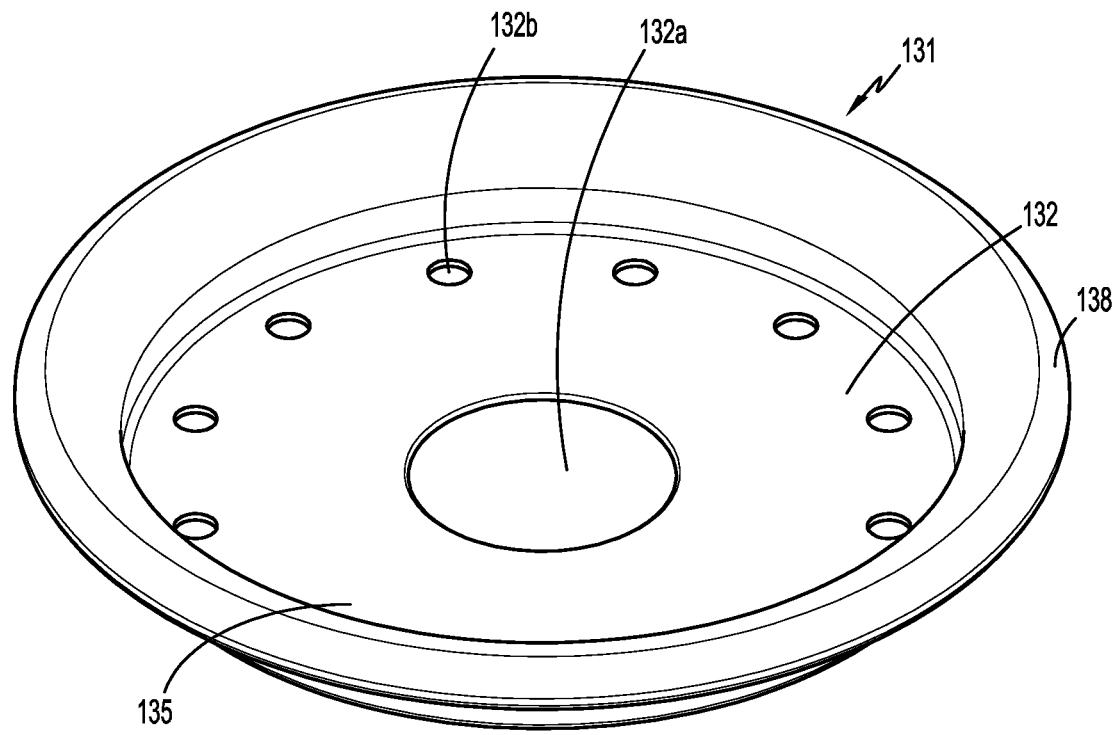
FIG. 5 is a top perspective view of a base seal member of a centering mechanism of the valve assembly of FIG. 3.
Figure 6:
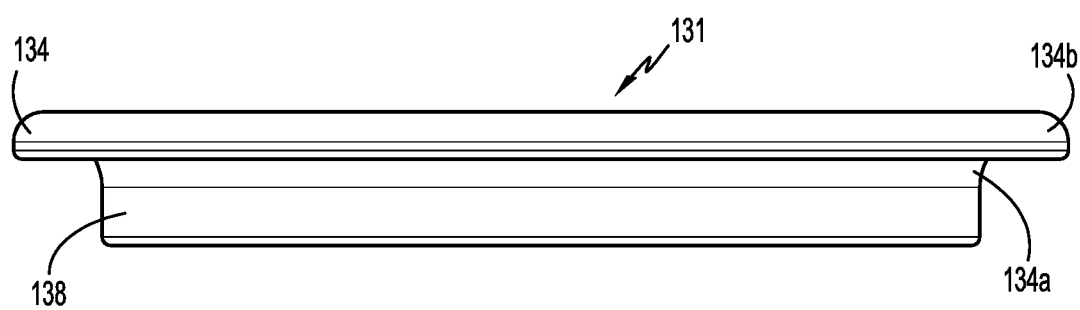
FIG. 6 is a side view of the base seal member of FIG. 5.

With reference to FIGS. 3-5, the valve assembly 120 in accordance with an embodiment of the present disclosure includes a centering mechanism 130, a guard assembly 140, a seal assembly 160, and a retainer frame assembly 180. The centering mechanism 130 is configured to bias the valve assembly 120 towards a generally centered position, i.e., concentrically positioned within a cavity 115 (FIG. 2) defined in the instrument valve housing 110. The centering mechanism 130 permits, e.g., radial, movement of the valve assembly 120 relative to the instrument valve housing 110 when the surgical instrument 10 is received through the valve assembly 120 and manipulated by a clinician. The centering mechanism 130 returns the valve assembly 120 to a generally centered position once the surgical instrument 10 is withdrawn from the instrument valve housing 110. The centering mechanism 130 is configured to engage various points of the upper housing section 112 to bias the centering mechanism 130 towards a generally centered position. In addition, the centering mechanism 130 is configured to engage at least two surfaces of the instrument valve housing 110 in a sealing relation when the centering mechanism 130 is radially off centered, as will be discussed below.

With additional reference to FIG. 4, the centering mechanism 130 includes a base seal member 131 and a radial retention member 170. The base seal member 131 includes an annular base 132 and a flange portion 138 extending from the annular base 132 such that the base seal member 131 defines a recess 135 configured to receive the guard assembly 140 therein. The annular base 132 defines a central opening 132a configured to receive the surgical instrument 10 therethrough, and a plurality of bores 132b circumferentially defined about the central opening 132a. The plurality of bores 132b is configured to receive respective pins 182 of a first member 181 of the retainer frame assembly 180, as will be discussed below.

Figure 7:
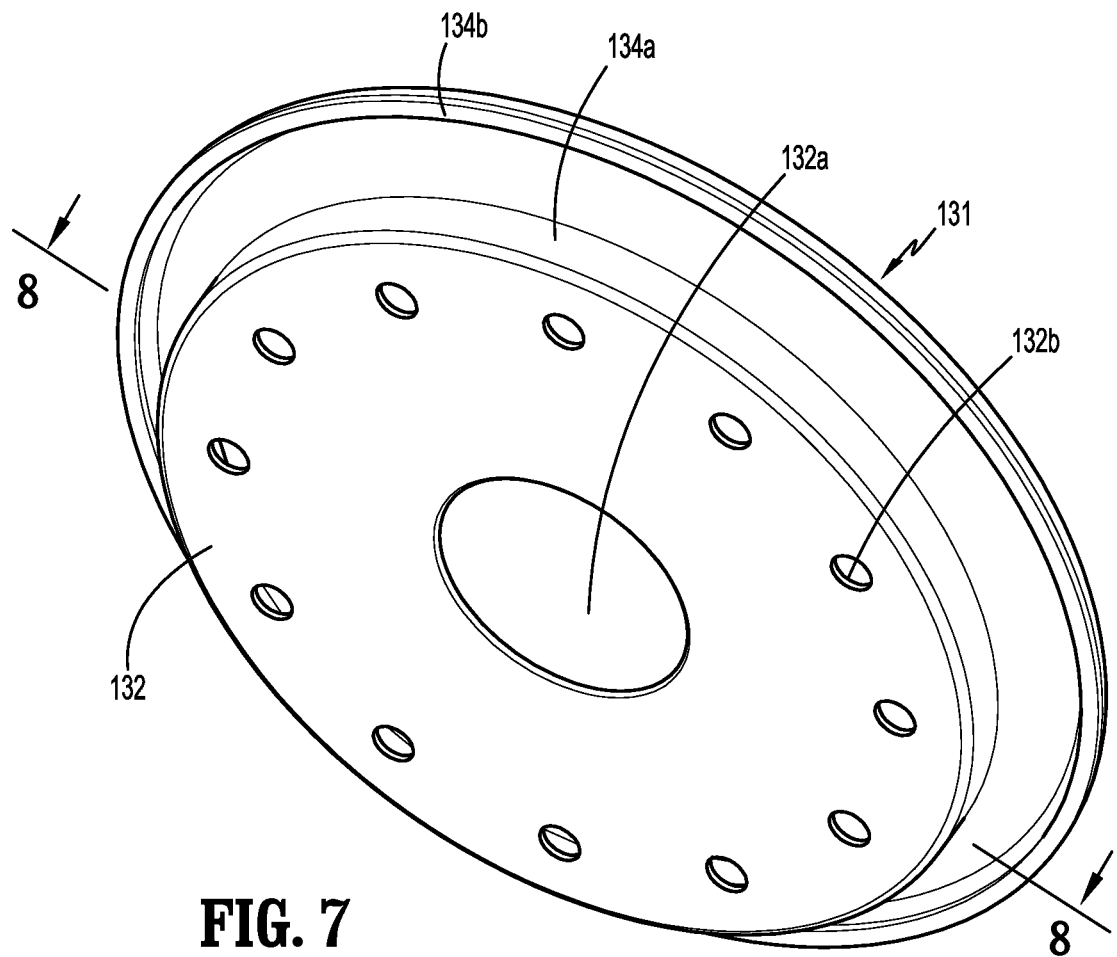
FIG. 7 is a bottom perspective view of the base seal member of FIG. 5.
Figure 8:
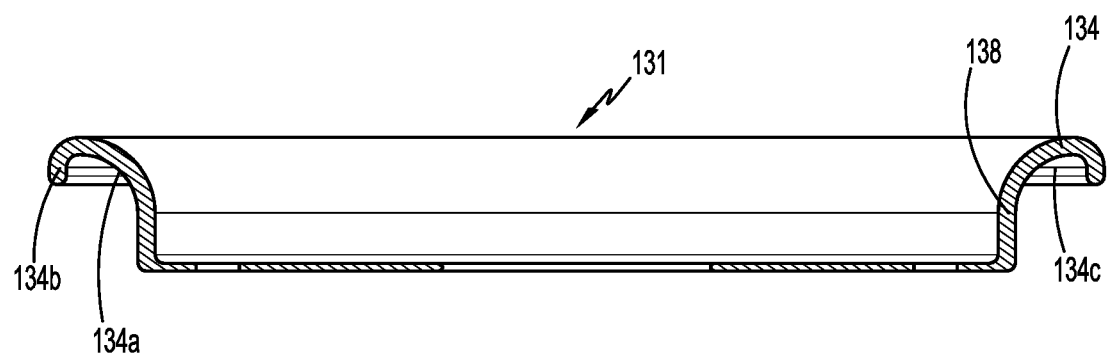
FIG. 8 is a side cross-sectional view of the base seal member of FIG. 5 taken along section line 8-8 of FIG. 7.

With reference to FIGS. 7 and 8, the flange portion 138 of the base seal member 131 includes an arcuate portion 134 extending radially outward. The arcuate portion 134 includes inner and outer segments 134a, 134b defining a gap 134c therebetween. Under such a configuration, the arcuate portion 134 is configured to adjustably engage a distal surface 112a (FIG. 2) of the upper housing section 112 in a sealing relation and maintain such contact during insertion and movement of the surgical instrument 10 in the longitudinal passage 111 (FIG. 2). A conventional base seal member may suffer from buckling or bending during movement thereof, which may result in a loss of sealing contact with the surgical instrument and/or the instrument valve housing. In contrast, the base seal member 131 engages the upper housing section 112 in a sealing relation during movement of the valve assembly 120 within the cavity 115. In particular, the arcuate portion 134 of the base seal member 131 adjustably engages the distal surface 112a of the upper housing segment 112 to enable sealing contact during, e.g., radial, movement in the cavity 115.

In addition, the arcuate portion 134 of the base seal member 131 is configured to adjustably engage a lateral surface 112b (FIG. 2) of the upper housing segment 112 in a sealing relation during an off-centered movement of the seal assembly 120. In particular, the gap 134c defined between the inner and outer segments 134a, 134b enables the arcuate portion 134 to adjustably engage the lateral surface 112b, as well as the distal surface 112a, of the upper housing section 112 in a sealing relation during movement of the valve assembly 120. Specifically, when the centering mechanism 130 comes to contact the lateral surface 112b of the upper housing section 112, the outer portion 134b of the arcuate portion 134 may deflect radially inward to maintain sealing contact with the upper housing section 112. Under such a configuration, the base seal member 131 of the centering mechanism 130 may engage the upper housing section 112 at multiple locations and enhance sealing relation with the upper housing section 112.

With reference back to FIGS. 3 and 4, the centering mechanism 130 further includes the radial retention member 170. The radial retention member 170 is configured to bias the off-centered valve assembly 120 towards a generally centered position within the cavity 115 (FIG. 2) of the instrument valve housing 110. Once the surgical instrument 10 is withdrawn from the valve assembly 120 that is radially displaced from a generally centered position, the radial retention member 170 returns the valve assembly 120 to the generally centered position. The radial retention member 170 includes an annular ring 172 and a plurality of spokes or spring elements 174 extending radially outward from the annular ring 172. Each spoke 174 may define a radius of curvature corresponding to a radius of curvature of the annular ring 172 such that when the spoke 174 is pressed against the lateral surface 112b (FIG. 2) of the upper housing section 112, the spoke 174 may wrap around the annular ring 172. Each spoke 174 includes a free end 174a normally biased to engage the lateral surface 112b of the upper housing section 112 of the instrument valve housing 110 (FIG. 1) when positioned within the cavity 115. In this manner, the centering mechanism 130 provides improved spring back for the valve assembly 120 when the valve assembly 120 is moved off-center.

With continued reference to FIGS. 3 and 4, the guard assembly 140 is configured to be disposed in the recess 135 defined in the base seal member 131, in a superposed relation with the annular base 132 (FIG. 5). The guard assembly 140 is configured to protect the seal assembly 160 during insertion and withdrawal of the surgical instrument 10 into and from the seal assembly 160. The guard assembly 140 includes a plurality of petals 144 arranged in a circular manner such that adjacent petals 144 are at least partially overlapped to enable slidable movement therebetween. The plurality of petals 144 defines a central opening 146. The petals 144 also operate to guide and orient the surgical instrument through the seal assembly 160. The central opening 146 is configured for receipt of the surgical instrument 10 therethrough. A peripheral portion 144a of each petal 144 defines bores 148. The plurality of bores 148 is configured to receive the respective pins 182 of the retainer frame assembly 180, as will be discussed below. In addition, the pins 182 secure the petals 144 relative to each other.

The guard assembly 140 may be formed from, e.g., a sheet of plastic/polymeric material, by stamping with a tool that forms the petals 144. The petals 144 are configured to flex distally (i.e., away from the first member 181 of the retainer frame assembly 180), upon engagement with the surgical instrument 10 to facilitate passage of the surgical instrument 10 through the seal assembly 160, which, in turn, stretches the seal assembly 160 to increase the size of a central opening 161 of the seal assembly 160. The increased size of the central opening 161 of the seal assembly 160 permits receipt of the surgical instrument 10 through the valve assembly 120.

It is envisioned that the guard assembly may include any number of petals and the petals may include flap portions of any size or configuration. For a detained description of a guard assembly, reference may be made to U.S. Pat. Nos. 5,895,377 and 6,569,120, and International Patent Publication No. WO 91/12838, the entire disclosures of which are all hereby incorporated by reference herein, for exemplary guard assemblies.

With respect to FIGS. 3 and 4, the seal assembly 160 of the valve assembly 120 is configured to provide a seal around an outer surface of the surgical instrument 10 passing through the instrument valve housing 110. The seal assembly 160 includes a plurality of seal segments 162 that are stackable to form a seal having a virtual inner circumferential surface defining an opening 161 to facilitate sealed passage of the surgical instrument 10 through the seal assembly 160. In embodiments, the opening 161 may be between about 0.025" and about 0.100" in diameter.

The seal assembly 160 defines a substantially planar, hexagonal member. The hexagonal shape facilitates assembly of the seal assembly 160, allowing for quick placement of the seal segments 162 in relation to each other, and/or by allowing for a quick visual check of the seal assembly 160 to ensure that the seal segments 162 are properly assembled. By forming the opening 161 out of multiple segments 162, i.e., forming a virtual inner circumferential surface, instead of having a continuous solid opening through a single seal member, the likelihood of the seal assembly 160 tearing during insertion, removal, and/or use of a surgical instrument therethrough is greatly reduced. Although six (6) segments shown, it is envisioned that the seal assembly 160 may include as few as, e.g., four (4) segments, and as many as, e.g., eight (8) segments.

The seal segments 162 of the seal assembly 160 may be formed of an elastic material, e.g., rubber, polyisoprene, or silicone elastomers. In one embodiment, the seal assembly 160 is formed of liquid silicon rubber (LSR). In embodiments, the seal segments 162 may include one or more fabric layers. Each seal segment 162 of the seal assembly 160 may be substantially wing-shaped and configured to partially overlap an adjacent seal segment 162 when the seal assembly 160 is in the assembled or stacked configuration. Each seal segment 162 includes a base portion 162*a* and a seal portion 162*b* extending from the base portion 162*a*. The base portion 162*a* and the seal portion 162*b* may be formed of the same or different material. The base portion 162*a* of the seal segment 162 defines a plurality of openings 163 to facilitate assembly and retention of the seal assembly 160 in the stacked configuration. More particularly, the plurality of openings 163 are configured to receive pins 182 of the retainer frame assembly 180, for securing the seal segments 162 relative to each other. In particular, the seal portion 162*b* of each seal segment 162 of the seal assembly 160 may taper radially inwardly to facilitate reception of a surgical instrument 10 through the seal assembly 160, and/or may enhance sealing about the surgical instrument 10.

In the assembled, or stacked configuration, the seal assembly 160 includes a substantially planar body having a substantially uniform thickness. It is envisioned that the aspects of the present disclosure may be modified for use with an access assembly having a substantially conical body. Misalignment of any one of the seal segments of the seal assembly 160 may compromise the integrity of the seal assembly 160. The configuration of the seal assembly 160 permits visual inspection of the seal assembly 160 to determine if the seal assembly 160 is assembled properly.

With continued reference to FIGS. 3 and 4, the retainer frame member 180 of the valve assembly 120 is configured to secure the guard assembly 140 relative to the seal assembly 160, and secure the guard and seal assemblies 140, 160 to the centering mechanism 130. The retainer frame member 180 includes the first member 181, a second member 185, and a third member 189. The first member 181 includes a plurality of pins 182 extending from a distal surface of the first member 181. The second member 185 defines an opening 184 concentrically arranged with the opening 161 of the seal assembly 160. The second member 185 defines a plurality of bores 186 circumferentially arranged and configured receive the plurality of pins 182 therethrough. The third member 189 defines an annular groove 189*a* configured to receive the plurality of the pins 182 of the first member 181 to secure first member 181 thereto. For example, the pins 182 may be frictionally received in the annular groove 189*a*. Alternatively, the pins 182 may be welded, glued, adhered, bonded or otherwise secured to the plurality of bores 186 in the second member 185 and the annular groove 189*a* in order to secure the first, second, and third members 181, 185, 189 together.

The plurality of pins 182 of the first member 181 extends through the respective bores 148 of the guard assembly 140 and the bores 132*b* (FIG. 5) of the base seal member 131 of the centering mechanism 130. The plurality of pins 182 further extends through the plurality of openings 163 of the seal assembly 160 and the plurality of bores 186 of the second member 185 such that the plurality of pins 182 is securely received within the annular groove 189*a* of the third member 189. Under such a configuration, the seal assembly 160 is interposed between the base seal member 131 of the centering mechanism 130 and the second member 185 of the retainer frame assembly 180. In particular, the third member 189 is dimensioned to be received within a central opening 175 defined in the radial retention member 170. The central opening 175 of the radial retention member 170 and a central opening 189*b* defined by the third member 185 of the retainer frame assembly 180 are concentrically arranged and are dimensioned to facilitate movement of the surgical instrument 10.

In use, the valve assembly 120 is initially positioned generally centered in the instrument valve housing 110 in the absence of the surgical instrument 10. The free ends 174*a* of the radial retention member 170 engage the lateral surface 112*b* (FIG. 2) of the upper housing section 112. At this time, the arcuate portion 134 of the base seal member 131 of the centering mechanism 130 engages the distal surface 112*a* of the upper housing section 112 in a sealing relation. As the surgical instrument 10 is introduced into the instrument valve housing 110 through the longitudinal passage 111 in the upper and lower housing sections 112, 114, the distal end of the surgical instrument 10 engages the petals 144 of the guard assembly 140 causing the respective petals 144 to flex distally towards the seal assembly 160. Such flexing of the petals 144 causes the central opening 161 of the seal assembly 160 to open to accommodate passage of the surgical instrument 10. In this manner, the guard assembly 140 protects the seal assembly 160 from tearing or other damage as the surgical instrument 10 is received through and withdrawn from the seal assembly 160.

Figure 9:
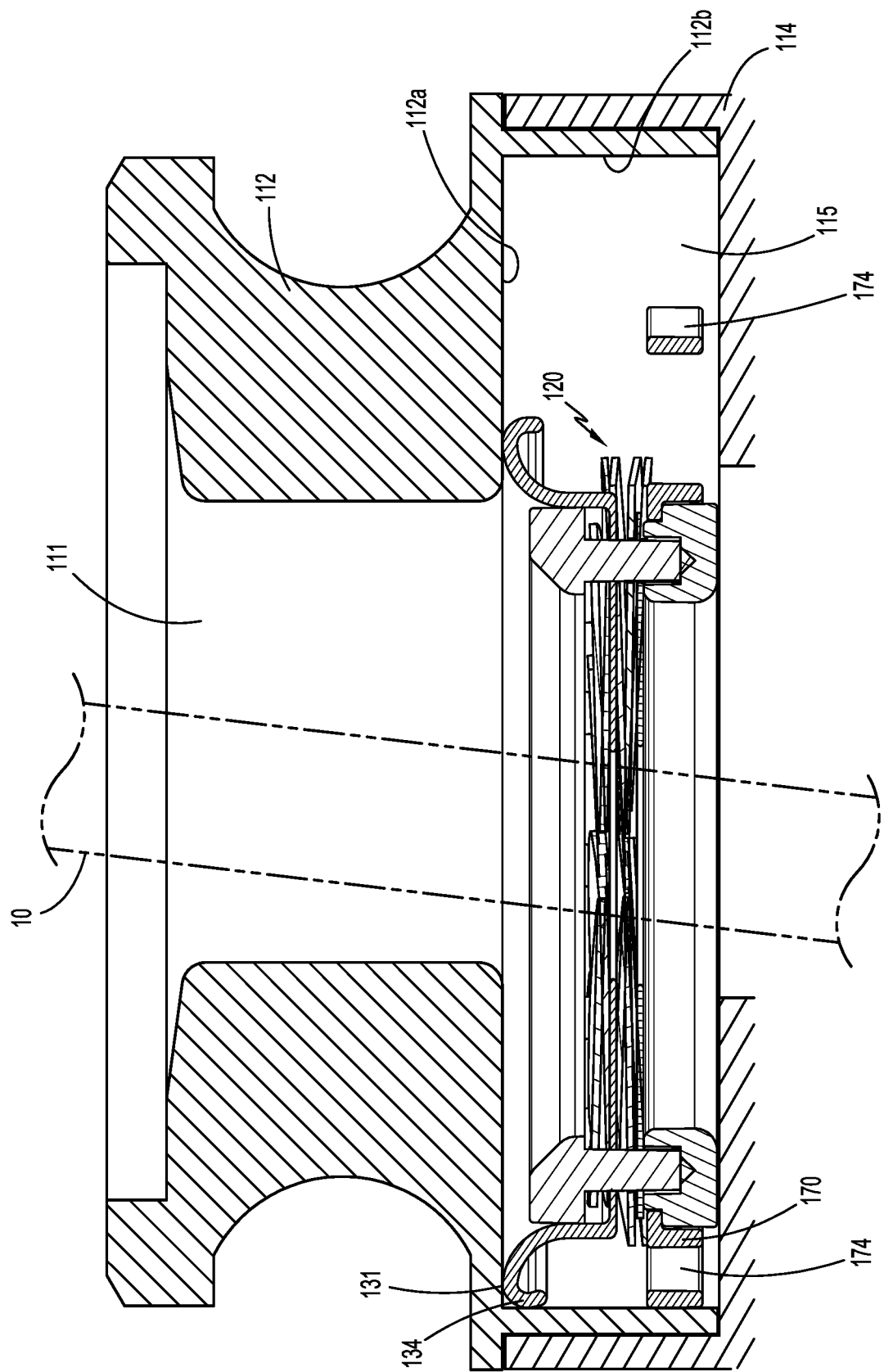
FIG. 9 is a side cross-sectional view of the surgical access assembly of FIG. 1 taken along section line 9-9 of FIG. 1, illustrating off-centered movement of the valve assembly.

When the clinician inserts the surgical instrument 10 into the valve assembly 120, the valve assembly 120 may move within the cavity 111. During a surgical procedure, the valve assembly 120 may be radially displaced such that some of the free ends 174*a* of the radial retention member 170 may be compressed and may wrap around the annular ring 172 of the radial retention member 170. At this time, the arcuate portion 134 of the base seal member 131 may engage the lateral surface 112*b* (FIG. 9), as well as the distal surface 112*a*, of the upper housing section 112 in a sealing relation. Once the surgical instrument 10 is withdrawn from the instrument valve housing 110, the centering mechanism 130 returns the valve assembly 120 to a generally centered position, while the arcuate portion 134 maintains sealing relation with the distal surface 112*a* of the upper housing section 112. The engagement of the arcuate portion 134 and the distal surface 112*a* helps maintain a pressure boundary across the valve assembly 120.

While various embodiments of the present disclosure have been shown and described herein, it will be obvious to those skilled in the art that these embodiments are provided by way of example only. Numerous variations, changes, and substitutions will now occur to those skilled in the art without departing from the present disclosure. Accordingly, it is intended that the invention be limited only by the spirit and scope of the appended claims.

What is claimed is:

1. A valve assembly usable in an access device, the valve assembly comprising:
a centering mechanism configured to bias the valve assembly towards a centered position in the access device, the centering mechanism including:
a base seal member having a flange portion, the flange portion including an arcuate portion configured to adjustably engage a first surface of the access device and a second surface of the access device in a sealing relation; and
a radial retention member having an annular ring and spokes circumferentially disposed about the annular ring, the spokes biased radially outwards;
a seal assembly attachable to the centering mechanism and configured to engage a surgical instrument in a sealing relation; and
a guard assembly attachable to the centering mechanism and configured to protect the seal assembly during insertion and manipulation of the surgical instrument, the guard assembly including petals defining a central opening and adjacent petals at least partially overlap in a circular manner to enable relative movement to enable enlarging the central opening.

2. The valve assembly of claim 1, wherein the first surface of the access device is orthogonal with respect to the second surface of the access device.

3. The valve assembly of claim 1, wherein the base seal member defines a recess configured to receive the guard assembly in a superposed relation.

4. The valve assembly of claim 1, wherein the arcuate portion includes an inner segment and an outer segment extending radially outwards from the inner segment, the inner segment and the outer segment defining a gap therebetween.

5. The valve assembly of claim 1, further including a retainer frame assembly configured to secure the seal assembly and the guard assembly with the centering mechanism.

6. The valve assembly of claim 5, wherein the retainer frame assembly includes a first member and a second member, the first member including pins extending through the guard assembly, the centering mechanism, and the seal assembly, and into the second member.

7. The valve assembly of claim 6, wherein the second member includes an annular groove configured to secure the pins of the first member.

8. The valve assembly of claim 1, wherein the seal assembly includes seal segments defining an opening configured to receive the surgical instrument in a sealing relation, the seal segments arranged about the opening in which adjacent seal segments are at least partially overlapped to enable relative movement between adjacent seal segments for adjustable engagement with the surgical instrument.

9. The valve assembly of claim 8, wherein respective peripheral portions of the guard assembly and the seal segments are secured with the base seal member of the centering mechanism.

10. A valve assembly for use in an access device comprising:
a retainer frame assembly including a first member and a second member;
a centering mechanism configured to bias the valve assembly towards a generally centered position within an instrument valve housing of the access device, the centering mechanism including:
a base seal member having:
an annular base; and
a flange portion including an arcuate portion configured to adjustably engage a first surface of the instrument valve housing and a second surface of the instrument valve housing of the access device in a sealing relation;
a seal assembly attachable to the centering mechanism and configured to engage a surgical instrument inserted through the valve assembly in a sealing relation; and
a guard assembly attachable to the base seal member and configured to protect the seal assembly during insertion and manipulation of the surgical instrument,
wherein the retainer frame assembly is configured to secure the seal assembly and the guard assembly with the centering mechanism and the retainer frame assembly includes a first member, a second member, and a third member, the first member including pins extending through the guard assembly, the centering mechanism, the seal assembly, and the second member, and into the third member.

11. The valve assembly of claim 10, wherein the first surface of the instrument valve housing is orthogonal with respect to the second surface of the instrument valve housing.

12. The valve assembly of claim 10, wherein the arcuate portion includes an inner segment and an outer segment that define a gap between the inner segment and the outer segment.

13. The valve assembly of claim 10, wherein the centering mechanism further includes an annular ring having spokes extending outwardly from the annular ring.

14. The valve assembly of claim 10, wherein the base seal member includes a third surface and a fourth surface that oppose each other and the seal assembly is secured to the third surface.

15. The valve assembly of claim 14, wherein the guard assembly is securable to the fourth surface.

16. The valve assembly of claim 10, wherein the third member includes an annular portion defining an annular groove that is configured to secure the plurality of pins of the first member.

17. A valve assembly comprising:
a centering mechanism configured to bias the valve assembly towards a centered position in a surgical access device, the centering mechanism including a base seal member having a flange portion, the flange portion including an arcuate portion configured to adjustably engage surfaces of the surgical access device in a sealing relation;
a seal assembly attachable to the centering mechanism and configured to engage a surgical instrument inserted into the valve assembly in a sealing relation, the seal assembly including seal segments defining an opening configured to receive the surgical instrument in a sealing relation, the seal segments arranged about the opening in which adjacent seal segments are at least partially overlapped to enable relative movement between adjacent seal segments for adjustable engagement with the surgical instrument;
a guard assembly attachable to the centering mechanism and configured to protect the seal assembly during insertion and manipulation of the surgical instrument; and a retainer frame assembly including pins extending through the guard assembly, the centering mechanism, and the seal assembly.

* * * * *